United States Patent [19]

Nakabayashi et al.

[11] Patent Number: 5,243,006
[45] Date of Patent: Sep. 7, 1993

[54] ACRYLIC COPOLYMER

[75] Inventors: Nobuo Nakabayashi, 6-20 Koganehara 5-chome, Matsudo-shi, Chiba, 270; Kazuhiko Ishihara, Tokyo; Takashi Yamamoto, Yamaguchi; Toru Kinoshita, Tokyo, all of Japan

[73] Assignees: Nobuo Nakabayashi, Chiba; Mitsui Petrochemical Industries, Ltd., Tokyo, both of Japan

[21] Appl. No.: 689,940

[22] PCT Filed: Oct. 2, 1990

[86] PCT No.: PCT/JP90/01266
§ 371 Date: May 31, 1991
§ 102(e) Date: May 31, 1991

[87] PCT Pub. No.: WO91/04994
PCT Pub. Date: Apr. 18, 1991

[30] Foreign Application Priority Data

Oct. 2, 1989 [JP] Japan .................................. 1-257298
Apr. 24, 1990 [JP] Japan .................................. 2-108280

[51] Int. Cl.$^5$ .................... C08F 212/14; C08F 220/12

[52] U.S. Cl. ................................... 526/286; 523/118; 526/240; 526/287

[58] Field of Search ................ 526/287, 286; 523/118, 523/116

[56] References Cited

U.S. PATENT DOCUMENTS 3,033,833 5/1962 Le Fevre .
4,373,056 2/1983 Besecke .
4,870,120 9/1989 Tsubakimoto .

*Primary Examiner*—Christopher Henderson
*Attorney, Agent, or Firm*—Sherman and Shalloway

[57] ABSTRACT

The acrylic copolymer of the present invention is an acrylic copolymer comprising recurring units derived from a (meth)acrylic ester compound and recurring units derived from a vinyl compound having —SO$_3$R (wherein R represents a hydrogen atom or a lower alkyl group) or having an acceptable salt thereof, wherein at least a part of ester groups of the (meth)acrylic ester compound is substituted by a group having recurring units derived from a (meth)acrylic ester. The present invention further provides a process for the preparation of the acrylic copolymer and use application of the acrylic copolymer utilizing its adhesion properties.

5 Claims, No Drawings

ACRYLIC COPOLYMER

FIELD OF THE INVENTION

The present invention relates to a novel acrylic copolymer, a process for the preparation of the acrylic copolymer and the use/application of the acrylic copolymer, and particularly to an adhesive composition containing the copolymer. In more detail, the invention relates to a novel acrylic copolymer having an excellent affinity for hydroxyapitite structures and having a high solubility or a high dispersibility in solvents, a process for the preparation of the acrylic copolymer and an adhesive composition containing the acrylic copolymer.

BACKGROUND OF THE INVENTION

For repairing or remedying hydroxyapitite structures such as dentin, (meth)acrylic resins for biochemical art (i.e., acrylic resins) having radical polymerizability have been conventionally employed. In such use application, it is required that an adhesive strength between the acrylic resins and the hydroxyapitite structures hardly varies for a very long period of time and the adhesive strength therebetween is high. Therefore, in the case of remedying dentin by the use of a remedying acrylic resin containing a methacrylic resin as an adhesive component, there has been employed a method comprising treating the beforehand-abraded (or beforehand-shaved) surface of the dentin with an etching agent such as an acid to remove shavings and to roughen the surface, then coating the surface with an adhesive containing a similar component to that of the remedying acrylic resin, then curing the coated adhesive, and coating the cured adhesive with the remedying acrylic resin.

However, the etching agent used in the roughening treatment, such as an acid, sometimes permeates inside of the aimed object to damage the hydroxyapitite structure, because the etching agent is a low-molecular compound. Further, if the hydroxyapitite structure is dentin, the etching agent permeates the structure to stimulate a nerve, and therefore the patient sometimes suffer an acute pain in the remedy.

In the conventional remedy for such parts, a cement prepared by combining a polyacrylic acid with zinc oxide or an aluminosilicate glass is applied on a surface of the hydroxyapitite structure and then the acrylic resin is applied thereon, to mitigate the stimulation in the adhering stage. However, such cement inherently has low adhesion properties, so that it is impossible to make a sufficient remedy by the use of the cement.

For the above-mentioned reason, the present inventors have proposed to employ a polymer-type surface-treating agent comprising an acidic group-containing polymer, in order to reduce a damage of the hydroxyapitite structure and to prevent the etching agent from permeation inside of the aimed object. (see: Japanese Patent Application No. 60(1985)-171024)

The acrylic copolymer described in this specification has a sulfonic acid group. Concretely, a copolymer of a methacrylic ester (e.g., methyl methacrylate) and a monomer containing a sulfonic acid group (e.g., a p-styrene sulfonic acid) is dissolved in a solvent such as water or ethanol, then the resulting solution is applied on a surface of the hydroxyapitite structure, and thus coated structure is washed with water. By the adaptation of this method, the surface treatment of the hydroxyapitite structure can be done with restraining invasion of the etching agent into the hydroxyapitite structure. Further, on the surface of the hydroxyapitite structure is formed a layer which is adsorbed with a copolymer used in this treatment. The copolymer layer firmly adheres to the hydroxyapitite structure, because the sulfonic acid group of the copolymer is bonded to the calcium component contained in the hydroxyapitite structure. Moreover, the copolymer layer has an excellent affinity for the adhesive acrylic resin (or remedying acrylic resin) which is to be applied on the layer, because the copolymer of the layer contains recurring units derived from methyl methacrylate Accordingly, in the case of using the acrylic copolymer, the hydroxyapitite structure and a filler are united with each other via the acrylic resin, and thereby the adhesion between the hydroxyapitite structure and the filler becomes excellent and this excellent adhesion can be kept for a long period of time.

However, the present inventors have further studied on the acrylic copolymer, and found that the affinity of the acrylic copolymer for the acrylic resin which is to be applied on the copolymer should be more improved although the adhesion of the copolymer to the hydroxyapitite structure is prominently high. For example, the adhesive strength of the copolymer varies depending upon a polymerization initiator contained in the acrylic resin.

If the content of the recurring units derived from a monomer having an excellent affinity for resins such as methyl methacrylate is increased by the conventional method in order to solve the above-mentioned problem, the resulting acrylic copolymer tends to lower in solubility in solvents and also tends to lower in adhesive strength to the hydroxyapitite structure. That is, it has been found that the aimed adhesive strength of the acrylic copolymer cannot be obtained by only adjusting the copolymer composition, namely, a ratio between methyl methacrylate and p-styrene sulfonic acid.

The object of the present invention is to provide a novel acrylic copolymer, a process for the preparation of the acrylic copolymer and use application of the acrylic copolymer.

In more detail, the object of the invention is to provide a novel acrylic copolymer which has excellent adhesion properties to both the hydroxyapitite structures and the acrylic resins containing an acrylic ester composition of radical polymerizability as a host adhesive component and also shows high solubility in solvents such as water and ethanol. Further, the object of the invention is to provide a process for the preparation of the acrylic copolymer and use application of the acrylic copolymer.

DISCLOSURE OF THE INVENTION

The acrylic copolymer of the invention is an acrylic copolymer comprising recurring units derived from a (meth)acrylic ester compound and recurring units derived from a vinyl compound having —$SO_3R$ (wherein R represents a hydrogen atom or a lower alkyl group) or having an acceptable salt thereof, wherein at least a part of ester groups of the (meth)acrylic ester compound is substituted by a group having recurring units derived from a (meth)acrylic ester.

In the acrylic copolymer of the invention, the recurring units derived from the (meth)acrylic ester are preferably recurring units having the formula [I]; the recurring units derived from a vinyl compound having —SO₃R (wherein R represents a group or an atom selected from a hydrogen atom, a lower alkyl group and an alkali metal atom) are preferably recurring units having the formula [II]; and the recurring units derived from a (meth)acrylic ester wherein a part of ester groups is substituted by a group having recurring units derived from a (meth)acrylic ester are preferably recurring units having the formula [III]:

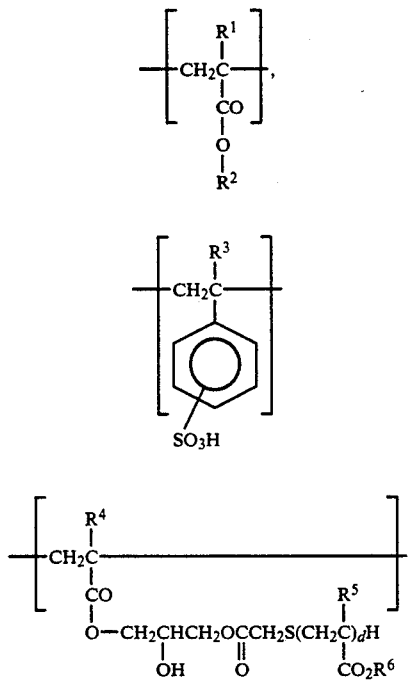

In the formulae [I] to [III], $R^1$, $R^3$, $R^4$ and $R^5$ each independently represent a hydrogen atom or an alkyl group having 1–5 carbon atoms; $R^2$ and $R^6$ each independently represent an alkyl group having 1–5 carbon atoms; and d represents an integer of from 1 to 300.

The process for the preparation of an acrylic copolymer according to the invention is characterized in that a mixture of a compound having the following formula I-a] and a compound having the following formula [III-a] is mixed with a compound having the following formula [II-a] in a molar ratio ranging from 95:5 to 5:95 to copolymerize with each other:

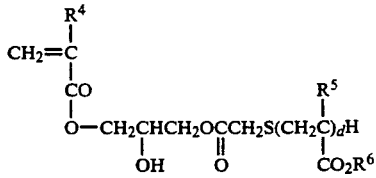

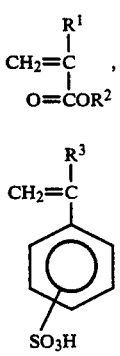

In the formulae [I-a] to [III-a], $R^1$, $R^2$, $R^3$, $R^4$, $R^5$, $R^6$ and d have the same meanings as defined above.

The adhesive composition of the invention and the dental adhesive composition of the invention are characterized in that they contain the above-mentioned acrylic copolymer.

As described above, the acrylic copolymer of the invention has specific recurring units, so that the copolymer not only shows high adhesion to hydroxyapatite but also shows excellent affinity for methacrylate compounds. Further, the acrylic copolymer having the above-mentioned structure exhibits high solubility in solvents.

Accordingly, the acrylic copolymer of the invention can be favorably employed as an adhesive for bonding acrylic resins to hydroxyapatite structures, especially as a dental adhesive.

PREFERRED EMBODIMENT FOR ACCOMPLISHING THE INVENTION

The acrylic copolymer of the invention, the process for the preparation of the acrylic copolymer and the use application of the acrylic copolymer will be concretely described hereinafter.

First of all, the acrylic copolymer of the invention is described referring to a preferred process for the preparation of the acrylic copolymer.

The acrylic copolymer of the invention can be obtained by polymerizing a monomer [A] capable of forming recurring units derived from a (meth)acrylic ester, a monomer [B] capable of forming recurring units derived from a vinyl compound having —SO₃R and a monomer [C] capable of forming recurring units derived from a (meth)acrylic ester bonded on the side chain with at least one group derived from a (meth)acrylic ester, utilizing known polymerization methods.

The monomer [A] used herein can be prepared by copolymerizing compounds having the following formula [I-a]:

$$\begin{array}{c} R^1 \\ | \\ CH_2=C \\ | \\ O=COR^2 \end{array} \quad [I\text{-}a]$$

In the formula [I-a], $R^1$ represents a hydrogen atom or an alkyl group having 1–5 carbon atoms. Concrete examples of the alkyl groups include a methyl group, an ethyl group, a propyl group, a butyl group and a pentyl group. $R^1$ is preferably an alkyl group, more preferably a methyl group.

$R^2$ is an alkyl group having 1–5 carbon atoms. Examples of the alkyl groups include a methyl group, an ethyl group, a propyl group, a butyl group and a pentyl group. $R^2$ is preferably a methyl group.

As preferred examples of the compounds having the formula [I-a] employable in the invention, there can be mentioned alkyl esters of (meth)acrylic acids such as methyl (meth)acrylate, ethyl (meth)acrylate, butyl (meth)acrylate, glycidyl (meth)acrylate, 2-hydroxyethyl (meth)acrylate and 3-hydroxypropyl(meth)acrylate. Of these, particularly preferred is methyl methacrylate.

The recurring unit derived from a vinyl compound having —SO$_3$R (wherein R has the same meaning as defined above) or having an acceptable salt thereof can be formed, for example, by polymerizing vinyl compounds or compounds obtained by bonding —SO$_3$R (wherein R has the same meaning as defined above) to vinyl compounds substituted by an alkyl group or the like directly or by way of other group.

Examples of the monomers containing a sulfonic acid group employable in the invention are sulfonic acid compounds having radical polymerizability (e.g., allyl sulfonic acid, methallyl sulfonic acid, vinyl sulfonic acid, p-styrene sulfonic acid, sulfoethyl-methacrylic acid and tert-butyl acrylamide sulfonic acid) and salts thereof (e.g., sodium salt and ammonium salt).

Among the above-mentioned compounds, preferred are compounds in which the above —SO$_3$R is indirectly bonded to a carbon atom constituting a vinyl group. A preferred example of such compounds is a compound having the following formula [II-a]:

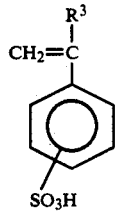

[II-a]

In the formula [II-a], R$^3$ represents a hydrogen atom or an alkyl group having 1–5 carbon atoms. Concrete examples of the alkyl groups include a methyl group, an ethyl group, a propyl group, a butyl group and a pentyl group. In the invention, R$^3$ is preferably a hydrogen atom.

In the compound having the formula [II-a], —SO$_3$R may be bonded at any position of orth-position, meta-position and para-position against another group on the benzene ring, but —SO$_3$R is preferably bonded at the para-position with respect to the reactivity with the hydroxyapatite structure. As a matter of course, the group represented by —SO$_3$R in the above formula may be an alkali metal atom such as a lithium salt, a potassium salt and a sodium salt, or may be an ammonium salt.

Preferred examples of the compounds having the formula [II-a] include sulfonic acid compounds having radical polymerizability (e.g., allyl sulfonic acid, methallyl sulfonic acid, vinyl sulfonic acid, p-styrene sulfonic acid, ethyl sulfomethacrylic acid and tert-butyl acrylamide sulfonic acid), sodium salts and ammonium salts thereof.

In the invention, other than the above-described method of copolymerizing monomers into which a sulfonic acid group has been beforehand introduced, there can be also utilized a method of polymerizing monomers not having a sulfonic acid group and then introducing a sulfonic acid group into the resulting polymer. Examples of the monomers employable in this method include α-olefins such as ethylene, propylene and butene-1; vinyl halides such as vinyl chloride; alkenyl benzenes such as styrene and α-methyl styrene; and (meth)acrylates such as ethyl (meth)acrylate. As compounds employable for introducing a sulfonic acid group into recurring units which are obtained by copolymerizing the above-mentioned monomers, there can be mentioned sulfuric acid, fuming sulfuric acid, liquid sulfurous acid, silver sulfate, triethyl phosphate/sulfur trioxide complex and long-chain acyl sulfate. In the invention, it is more preferred to employ a method of performing copolymerization using monomers having a sulfonic acid group than a method of copolymerizing monomers and then introducing a sulfonic acid group into the resulting polymer.

The acrylic copolymer of the invention can be obtained by copolymerizing two kinds of the above-mentioned monomers with a (meth)acrylic ester compound in which at least one group derived from a (meth)acrylic ester is bonded on the side chain.

As the acrylic ester compound, there can be mentioned for example a compound having the following formula [III-a]:

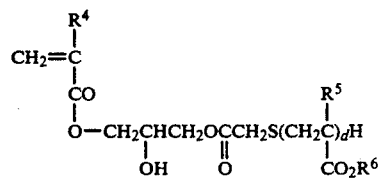

[III-a]

In the formula [III-a], R$^4$ and R$^5$ each independently represent a hydrogen atom or an alkyl group having 1–5 carbon atoms. Concrete examples of the alkyl groups include a methyl group, an ethyl group, a butyl group and a pentyl group. R$^4$ is preferably an alkyl group, particularly preferably a methyl group.

Further, at least any one of R$^1$ in the aforementioned [I-a] and R$^4$ is preferably a methyl group.

R$^5$ is an alkyl group having 1–5 carbon atoms, preferably an alkyl group having 1–3 carbon atoms. Examples of the alkyl groups include a methyl group, an ethyl group, a propyl group, a butyl group and a pentyl group. R$^5$ is preferably a methyl group.

R$^6$ is an alkyl group having 1–5 carbon atoms. Examples of the alkyl groups include a methyl group, an ethyl group, a propyl group, a butyl group and a pentyl group. R$^6$ is preferably a methyl group.

Furthermore, d in the above formula is an integer of from 1 to 300, preferably an integer of from 1 to 150, more preferably an integer of from 10 to 100.

The compound having the formula [III-a] can be prepared, for example, by causing a polymer having the formula [III-c] obtained by polymerizing methyl methacrylate through a chain transfer polymerization using thioglycolic acid to react with a compound having the following formula [III-b]:

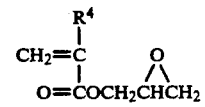

[III-b]

In the formula [III-b], R$^4$ has the same meaning as defined above.

Concrete examples of such compounds include glycidyl acrylate and glycidyl methacrylate.

A compound which forms the compound having the formula [III] employable in the invention by the reaction with the above-mentioned glycidyl compound is, for example, a compound having the formula [III-c]:

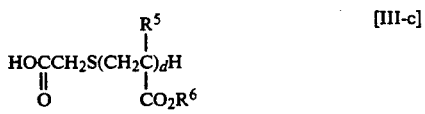

[III-c]

In the formula [III-c], $R^5$, $R^6$ and d have the same meanings as defined above.

The compound having the formula [III-b] and the compound having the formula [III-c] are caused to react with each other in the conventional manner, to synthesize the compound having the formula [III-a] employable in the invention. The size of the side chain, that is concretely, a value of d, can be controlled by changing the ratio between methyl methacrylate and a chain transfer-agent such as thioglycolic acid in the polymerization stage.

The compounds having the formulae [I-a], [II-a] and [III-a] can be polymerized with each other according to known methods for synthesizing graft polymers such as radical polymerization and ion polymerization. Those methods are described, for example, in "Polymer Material Design", edited by Polymer Institute.

In this case, a molar ratio between the monomer having the formula [II-a] and a mixture of the monomer having the formula [I-a] and the monomer having the formula [III-a] is generally in the range of 95:5 to 5:95, preferably in the range of 90:10 to 50:50. Further, the monomer having the formula [I-a] is generally used in an amount of 0 to 90% by mole, preferably 0 to 50% by mole, more preferably 0 to 40% by mole, based on the amount of the monomer having the formula [II-a].

There is no specific limitation on the reaction conditions for synthesizing the acrylic copolymer using the above-mentioned monomers. For example, the acrylic copolymer of the invention can be prepared at a temperature of from room temperature to 300° C. for a period of time of from 1 minute to 24 hours, preferably 1 minute to 10 hours, in a reaction solvent such as dimethylformamide.

The acrylic copolymer prepared as above has a molecular weight measured based on GPC in terms of polystyrene of generally not less than 100,000, preferably not less than 300,000, more preferably not less than 500,000, most preferably not less than 1,000,000.

In the process of the invention, other than the above-mentioned monomers, there can be also copolymerized various monomers such as acids (e.g, acrylic acids, methacrylic acids, itaconic acids, maleic acids, methacryloyloxybenzoic acids, N(2-hydroxy-3-methacryloyloxypropyl)-N-phenylglycine and 4-methacryloxyethyltrimellitic acid), anhydrides of those acids, and (meth)acrylic acid esters having alkyl amine (e.g., N,N-dimethylaminoethyl(meth)acrylate and N,N-diethylaminoethyl(meth)acrylate), provided that the use of those monomers does not mar the properties of the resulting copolymer. Utilizing recurring units derived from such monomers, a sulfonic acid group or a (meth)acrylic acid ester group can be introduced into the copolymer.

Examples of other substances which can be introduced into the copolymer of the invention include olefins such as ethylene, propylene and butene-1; vinyl halides such as vinyl chloride and vinyl bromide; vinyl esters such as vinyl acetate and vinyl propionate; vinyl ethers such as methyl vinyl ether, ethyl vinyl ether and isobutyl vinyl ether; and alkenylbenzenes such as styrene, vinyl toluene, α-methylstyrene, chloromethylstyrene and stilben.

The acrylic copolymer of the invention has a sulfonic acid group, so that the copolymer not only has an excellent affinity for the hydroxyapatite structures but also shows a high solubility or dispersibility in solvents such as water and alcohol. As the solvent used herein, there can be mentioned polar solvents. Especially in the case of adapting the acrylic copolymer to dental use, water, ethanol and a mixture solvent of water and ethanol are preferably employed as the solvent. The acrylic copolymer is generally dissolved in such solvents in an amount of 0.1 to 20% by weight, preferably 1 to 15% by weight.

To the acrylic copolymer solution, a metallic ion may be added. By addition of the metallic ion to the acrylic copolymer solution, the dispersibility of the acrylic copolymer in the solvent can be prominently improved, and further the adhesion between the acrylic copolymer and a dental composite to be coated on the acrylic copolymer can be enhanced. As the metallic ion, monovalent metallic ions such as sodium and potassium can be employed, but polyvalent metallic ions such as calcium, iron, copper, nickel, alminum and chromium can be preferably added. Of these polyvalent metallic ions, particularly preferred are calcium, iron, copper and aluminum.

The metallic ion is added to the acrylic copolymer solution in such a manner that not less than 50%, preferably not less than 30%, more preferably 10–20%, of the sulfonic acid groups constituting the acrylic copolymer would remain in the state of an acid.

The acrylic copolymer solution prepared as above can be employed as a surface-treating agent, an adhesive, etc. for structures containing a calcium component.

As examples of the structures containing the calcium component, there can be mentioned the structures containing calcium carbonate including calcite, Iceland spar, pagodite, limestone, marble, chalk and shell; the structures containing calcium phosphate including phosphor lime; the structures containing hydroxyapatite component including bone and dentin; and the structures containing calcium sulfate including gypsum. Preferred are compositions containing calcium carbonate or calcium phosphate as the calcium component, and more preferred are compositions containing calcium phosphate as the calcium component.

The structure containing such calcium component is coated with a solution of the acrylic copolymer of the invention, and then the structure coated with the solution is subjected to washing with water or solvent-removing treatment, whereby chemical bonding is formed between the sulfonic acid and the calcium component. Hence, the acrylic copolymer loses its solubility in solvents such as water and alcohol to form a cured layer on the surface of the structure.

This cured layer of the acrylic copolymer shows an excellent affinity for acrylic resins or the like by action of the side chain having a specific structure, as well as having excellent adhesion properties to the structures containing calcium components. Hence, when a dental composite is coated on the cured layer, the cured layer favorably serves as an adhesive layer for bonding dentin to the composite.

EFFECT OF THE INVENTION

The acrylic copolymer of the invention has a sulfonic acid group and a side chain of an acrylic ester, so that the copolymer shows a great affinity for both of a structure containing a calcium component and an acrylic resin having radical polymerizability. Further, the acrylic copolymer of the invention shows high solubility in solvents such as water and alcohol, so that in the case of treating a structure containing a calcium component with a solution of the acrylic copolymer and then coating thus treated structure with an acrylic resin, the structure containing a calcium component can be favorably bonded with the acrylic resin.

Accordingly, the acrylic copolymer of the invention can be favorably employed as a surface-treating agent for dentin or the like.

EXAMPLE

The present invention is further described by the following examples, but those examples are given by no means to restrict the invention.

Example 1

0.84 g of polymethyl methacrylate (AA-6, available from Toa Gosei Co., Ltd.) having a methacryloyloxy group at one terminal end of its molecule, 2.6 g of sodium p-styrenesulfonate (SSNa) and 0.034 g of AIBN were mixed with 30 ml of dimethylformamide (DMF), and they were subjected to polymerization at 70° C. for 19 hours in a glass ampoule.

The ampoule was unsealed, and the reaction product was introduced into acetone of large amount to obtain a copolymer. The copolymer was dried, and then using the dried copolymer, a 5% aqueous solution of the copolymer was prepared. To the solution was added 2.1 ml of 6N HCl, and the resulting solution was introduced into a dialyzing tube to dialyze the solution for 3 days. Then, water was removed from the resulting polymer solution, to obtain 2 g of an acrylic copolymer (gMS). As a result of measurement of the obtained copolymer by means of gel permeation chromatography (GPC) using N,N-dimethylformamide as a solvent, it was confirmed that the copolymer had one peak (molecular weight in terms of polystyrene: not less than 300,000).

Further, it was also confirmed from the infrared spectrum (IR) that the copolymer contained MMA and a styrenesulfonic acid unit.

Example 2

2 g of MMA, 8 g of AA-6, 20.6 g of SSNa and 0.36 g of AIBN were added to 220 ml of DMF in a flask, and they were stirred in the flask to perform polymerization at 70° C. for 21 hours.

The obtained polymerization reaction liquid was introduced into acetone of large amount to obtain a sodium salt of a copolymer. Then, using the obtained polymer salt, a 5% aqueous solution of the polymer salt was prepared. To the aqueous solution was added 16.6 ml of 6N HCl, and the resulting solution was introduced into a dialyzing tube to dialyze the solution for 3 days. Thereafter, water was removed from the resulting polymer solution through distillation, to obtain 14.4 g of an acrylic copolymer (rgMS).

It was confirmed from the above-mentioned GPC and IR that the obtained copolymer had MMA and a styrenesulfonic acid unit.

Example 3

In a three-necked flask, 200 g of MMA, 45.8 g of thioglycolic acid (TGA) ([TGA]/[MMA]=0.25) and 3.2 g of AIBN (1% by mole/MMA) were dissolved in 200 ml of THF, and they were subjected to polymerization at 60° C. for 3 hours in an atmosphere of argon gas.

The obtained polymerization reaction liquid was introduced into petroleum ether of large amount to obtain a prepolymer, and the obtained prepolymer was freeze-dried using benzene. The weight-average molecular weight of the prepolymer (Formula [III-c]) measured according to the above-mentioned GPC was 3,820 in terms of polystyrene.

Then, the prepolymer and glycidyl methacrylate (GMA) in an amount of 2.1 times of the molar amount of the prepolymer were dissolved in approx. 200 ml of xylene, and then a hydroquinone monoethyl ether (2% by mole of the prepolymer) and N,N-dimethyldodecylamine (1.5% by mole of the prepolymer) were further dissolved in the above-obtained solution, to cause them to react with each other at 140° C. for 8 hours in an atmosphere of argon gas. The polymerization reaction liquid was introduced into petroleum ether of large amount to obtain a polymer, and the obtained polymer was freeze-dried using benzene.

It was confirmed from the above-mentioned GPC, IR and $^1$H-NMR that the obtained polymer was a macromonomer having the formula [III-a].

Thereafter, 4.8 g of the macromonomer, 6.6 g of sodium styrenesulfonate (SSNa) and 28 mg of AIBN were dissolved in 20 ml of DMF in a glass ampoule, to perform polymerization at 70° C. for 18 hours in an atmosphere of argon gas.

The resulting polymerization reaction liquid was introduced into acetone of large amount to remove the unreacted macromonomer from the reaction liquid, so as to obtain a precipitate.

The precipitate was subjected to vacuum drying, and using the dried precipitate, a 5% aqueous solution was prepared. To the solution was added 5.3 ml of 6N HCl, and they were stirred for approx. 1 hour. The resulting solution was introduced into a dialyzing tube made of cellulose to dialyze the solution for 3 days using deionized water. Thereafter, water was removed from the resulting polymer solution through distillation, to obtain an aimed acrylic copolymer.

It was confirmed from the above-mentioned GPC that the obtained polymer had one peak. It was also confirmed from the above-mentioned IR that the obtained polymer had MMA and a styrenesulfonic acid unit.

Example 4

A prepolymer and a macromonomer were sequentially synthesized in the same manner as described in Example 3 except that the polymerization scale of a prepolymer was set to 1/20 of that of Example 3 and the ratio of [TGA]/[MMA] was changed to 0.75.

Using the obtained macromonomer, an acrylic copolymer was synthesized in the same manner as described in Example 3 except that the monomers were charged in such a manner that the unit molar fraction between MMA and SSNa would be 0.6:0.4.

Example 5

A prepolymer was synthesized in the same manner as described in Example 4 except that the ratio of

[TGA]/[MMA] was changed to 0.50. An acrylic copolymer derived from the obtained prepolymer was synthesized in the same manner as described in Example 4.

Example 6

The procedures of Example 4 were repeated except for changing the ratio of [TGA]/[MMA] to 0.25, to synthesize an acrylic copolymer.

Examples 7-16

An extracted fresh cattle tooth was abraded with a water-resistant emery paper of #600 under pouring of water. Thus abraded cattle tooth was coated with 40 μl of a solution containing an acrylic copolymer and ferric chloride at predetermined concentrations. The cattle tooth coated with the solution was left at rest for 6 seconds and then sufficiently washed with water to remove a soluble acrylic copolymer, so as to form a film of an insoluble acrylic copolymer on the surface of the cattle dentin.

The cattle dentin having the copolymer film thereon was dried at room temperature for 10 minutes, and then a double-sided adhesive tape having a hole of a diameter of 5.4 mm was attached to the acrylic copolymer film of the cattle dentin to determine the area where a resin is to be coated. On the hole of the attached tape was placed an acrylic ring having an inner diameter of 6 mm and a height of 1 mm. Into the acrylic ring was charged a dental resin for polymerizing MMA with a polymerization initiator consisting of a combination of tri-n-butylboran or BPO and dimethyl-p-toluidine (DMPT) (MMA-TBB resin or MMA-BPO-DMPT resin), and the cattle dentin with the dental resin was left at rest for 30 minutes at room temperature to cure the resin. The cattle dentin with the cured dental resin was immersed in water of 37° C. for 24 hours, and thereafter an acrylic bar (diameter: 6 mm) was caused to stand up on the dental resin using the MMA-BPO-DMPT resin. The adhesive strength between the dentin and the dental resin was measured using an autographic device (produced by Shimazu Seisakusho Co., Ltd.) at a cross head speed of 2 mm/min.

Comparative Examples 1-5

An extracted fresh cattle tooth was abraded with a water-resistant emery paper of #600 under pouring of water. Onto the surface of thus abraded cattle tooth was attached a double-sided adhesive tape having a hole of a diameter of 5.4 mm to determine the area where a resin is to be coated. On the hole of the attached tape was placed an acrylic ring having an inner diameter of 6 mm and a height of 1 mm. Into the acrylic ring was charged a commercially available high-molecular type cement, and the cement was cured. The cured cement was then coated with the MMA-TBB resin. Then, the adhesive strength between the dentin and the cement was measured in the same manner as described in Examples 7 to 14. The above-mentioned high-molecular type cement was prepared using Hybond Glass Ionomer (HYG, available from Matsukaze Co., Ltd.) and Ketack Cement (KC, available from ESPE Co., Ltd.) through a process directed by their makers.

Comparative Examples 6-15

The procedures of any of Examples 7 to 14 were repeated except for using polymer-type surface-treating agents not having the aforementioned formula [III] for comparison with the acrylic copolymer of the invention.

The compositions of the polymer-type surface-treating agents were as follows.

| Polymer Code | Composition of Copolymer Unit Molar Fraction | | Molecular Weight $Mn(10^4)$ |
| --- | --- | --- | --- |
| | MMA | SSA | |
| G | 0.35 | 0.65 | >100 |
| H | 0.75 | 0.25 | 85 |

SSA: p-styrenesulfonic acid

As shown in the above, for restraining a damage of the hydroxyapatite structure, the high-molecular type dentin bonding materials were tried to bond the structure to the repairing material. As a result, the commercially available materials (Comparative Examples 1 to 6) had an adhesive strength of approx. 0 to 0.3 MPa and were hardly bonded to the structure. However, in the case of using the acrylic copolymers of the invention, an excellent adhesive strength of 2.5 to 6.0 MPa was obtained. In the case of using the conventional polymer-type dentin surface-treating agents, the adhesive strength to the stimulation-sensitive dentin was 0 to 2.7 MPa. However, in the case of using the acrylic copolymers of the invention, the adhesive strength thereto was 2.7 to 3.2 MPa, that is, the adhesive strength was improved. Accordingly, the hydroxyapatite structures such as dentin were able to be repaired more reliably and more safely.

| Example No. | Prepolymer [TGA]/[MMA] | Result of Synthesis of Acrylic Copolymer | | | | | |
| --- | --- | --- | --- | --- | --- | --- | --- |
| | | Macromonomer | Acrylic Copolymer | | | | |
| | | Molecular Weight *1 (Mw) | Unit Molar Fraction of MMA | Molecular Weight *1 (Mw) | Yield (%) | CODE | |
| 1 | — | 12000 | 0.34 | >$10^6$ | 58 | A | |
| 2 | — | 12000 | 0.39 | >$10^6$ | 66 | B | |
| 3 | 0.25 | 3820 | 0.34 | >$10^6$ | 55 | C | |
| 4 | 0.75 | 2380 | 0.28 | >$10^6$ | 60 | D | |
| 5 | 0.50 | 3010 | 0.30 | >$10^6$ | 58 | E | |
| 6 | 0.25 | 5600 | 0.35 | >$10^6$ | 70 | F | |

*1: Molecular weight in terms of polystyrene measured based on GPC

| Example No. | Treating Agent | | | Dental Resin | Cattle Tooth | Adhesive Strength (MPa) |
| --- | --- | --- | --- | --- | --- | --- |
| | Acrylic Copolymer | Concentration (%) | $FeCl_3$ | | | |
| 7 | A | 3 | — | MMA-TBB | enamel | 5.7 |

-continued

| Example No. | Treating Agent | | | Dental Resin | Cattle Tooth | Adhesive Strength (MPa) |
|---|---|---|---|---|---|---|
| | Acrylic Copolymer | Concentration (%) | FeCl₃ | | | |
| 8 | A | 3 | 0.5 | MMA-TBB | enamel | 5.8 |
| 9 | A | 3 | — | MMA-BPO.DMPT | enamel | 3.4 |
| 10 | A | 3 | 0.5 | MMA-BPO.DMPT | enamel | 2.5 |
| 11 | C | 3 | — | MMA-BPO.DMPT | enamel | 6.0 |
| 12 | D | 3 | — | MMA-BPO.DMPT | enamel | 3.6 |
| 13 | E | 3 | — | MMA-BPO.DMPT | enamel | 3.0 |
| 14 | F | 3 | — | MMA-BPO.DMPT | enamel | 2.7 |
| 15 | E | 10 | 1.6 | MMA-TBB | dentin | 3.2 |
| 16 | F | 10 | 1.6 | MMA-TBB | dentin | 2.8 |

*¹: Molecular weight in terms of polystyrene measured based on GPC

| Comp. Ex. No. | High Molecular-type Cement | Dental Resin | Cattle Tooth | Adhesive Strength (MPa) |
|---|---|---|---|---|
| 1 | HYG | MMA-TBB | enamel | 0.1 |
| 2 | KC | MMA-TBB | enamel | 0.3 |
| 3 | EC | MMA-TBB | dentin | 0.2 |
| 4 | HYC | MMA-TBB | dentin | 0 |
| 5 | KC | MMA-TBB | dentin | 0.2 |

| Comp. Ex. No. | Polymer-type Surface Treating Agent | | | Dental Resin | Cattle Tooth | Adhesive Strength (MPa) |
|---|---|---|---|---|---|---|
| | Polymer | Concentration (%) | FeCl₃ | | | |
| 6 | — | — | — | MMA-TBB | enamel | 0.8 |
| 7 | — | — | — | MMA-TBB | dentin | 0.6 |
| 8 | G | 3 | — | MMA-TBB | enamel | 3.4 |
| 9 | G | 3 | 0.5 | MMA-TBB | enamel | 4.0 |
| 10 | H | 3 | — | MMA-TBB | enamel | 3.9 |
| 11 | H | 3 | 0.5 | MMA-TBB | enamel | 5.9 |
| 12 | G | 3 | — | MMA-TBB | dentin | 0 |
| 13 | G | 3 | 1.6 | MMA-TBB | dentin | 2.7 |
| 14 | H | 3 | — | MMA-TBB | dentin | 0 |
| 15 | H | 3 | 1.6 | MMA-TBB | dentin | 1.4 |

Example 17

Methyl methacrylate, thioglycolic acid and azoisobutylonitrile were mixed with each other to prepare a compound (macromonomer) having the formula [III-a]. In the mixing procedure, methyl methacrylate, thioglycolic acid and azoisobutylonitrile were employed in such amounts that the value of d in the aforementioned formula [III-a] would be 25.

Subsequently, to 30 ml of dimethylformamide were added styrenesulfonic acid (70% by mole) and a mixture of the above-mentioned macromonomer and methyl methacrylate (30% by mole, in terms of methacrylate unit constituting a main chain), to cause them to react with each other at 60° C. for 17 hours.

The reaction liquid was then introduced into acetone of excessive amount to obtain deposited crystals through filtration.

The obtained crystals were sufficiently dried, and then to the dried crystals was added water to prepare a 5% solution. To the solution was added a hydrochloric acid little by little under stirring, and the resulting solution was stirred for 2 hours to neutralize sodium. Thus prepared copolymer was purified for 3 days using a cellulose dialysis membrane, and then water was removed from the copolymer under reduced pressure to obtain an acrylic copolymer.

When the acrylic copolymer was measured on the molecular weight by means of GPC, the molecular weight of the copolymer was 1,500,000 in terms of polystyrene.

Then, 1 part by weight of the above-obtained acrylic copolymer and 99 parts by weight of ethanol were mixed with each other. Further, to the resulting mixture was added iron ion in the form of ferric chloride in such an amount that approx. 50% of the sulfonic acid groups contained in the acrylic copolymer was neutralized, and they were sufficiently stirred to prepare a homogeneous solution.

The solution was applied on a surface of a cattle tooth, and ethanol was removed from the coated solution to form a cured film of the acrylic copolymer on the surface of the cattle tooth.

Thereafter, a commercially available dental composite was applied on the cured film and the composite was cured. As a result, both the adhesion between the cattle tooth and the cured film of the acrylic copolymer and the adhesion between the cured film of the acrylic copolymer and the cured composite were sufficiently high.

We claim:

1. An acrylic copolymer comprising:
   recurring units from a (meth)acrylic ester having the formula (I), and
   recurring units from a vinyl compound having an —SO₃R group of the formula (II), wherein R is a hydrogen atom, a lower alkyl group or an alkali metal atom,
   wherein at least a part of alkyl groups of said recurring units from a (meth)acrylic ester are substituted by a group having recurring units from a (meth)acrylic ester and have the formula (III)

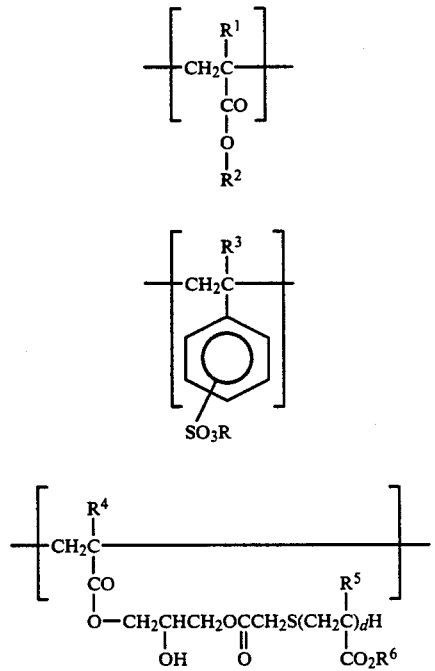

wherein $R^1$, $R^3$, $R^4$ and $R^5$ each independently represent a hydrogen atom or an alkyl group having 1–5 carbon atoms, $R^2$ an $R^6$ each independently represent an alkyl group having 1–5 carbon atoms, and d represents an integer of from 1 to 300.

2. An adhesive composition comprising an acrylic polymer, said acrylic polymer comprising:
recurring units from a (meth)acrylic ester having the formula (I), and
recurring units from a vinyl compound having an —SO₃R group of the formula (II), wherein R Is a hydrogen atom, a lower alkyl group or an alkali metal atom,
wherein at least a part of alkyl groups of said recurring units from a (meth)acrylic ester are substituted by a group having recurring units from a (meth)acrylic ester and have the formula (III)

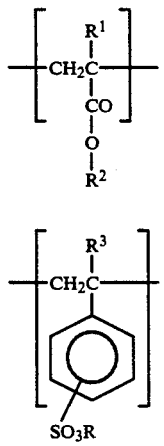

wherein $R^1$, $R^3$, $R^4$ and $R^5$ each independently represent a hydrogen atom or an alkyl group having 1–5 carbon atoms, $R^2$ and $R^6$ each independently represent an alkyl group having 1–5 carbon toms, and d represents an integer of from 1 to 300.

3. A dental adhesive composition comprising an acrylic polymer, said acrylic polymer comprising:
recurring units form a (meth)acrylic ester having the formula (I), and
recurring units from a vinyl compound having an —SO₃R group of the formula (II), wherein R is a hydrogen atom, a lower alkyl group or an alkali metal atom,
wherein at least a part of alkyl groups of said recurring units from a (meth)acrylic ester are substituted by a group having recurring units from a (meth)acrylic ester and have the formula (III)

wherein $R^1$, $R^3$, $R^4$ and $R^5$ each independently represent a hydrogen atom or an alkyl group having 1–5 carbon atoms, $R^2$ and $R^6$ each independently represent an alkyl group having 1–5 carbon atoms, and d represents an integer of from 1 to 300.

4. The acrylic copolymer as claimed in claim 1, wherein the number-average molecular weight of the acrylic copolymer is not less than 300,000.

5. The acrylic copolymer as claimed in claim 1, wherein at least one of $R^1$ and $R^4$ is a methyl group.

* * * * *